US012780900B2

(12) United States Patent
Zhang et al.

(10) Patent No.: US 12,780,900 B2
(45) Date of Patent: Nov. 3, 2026

(54) TRUNCATED BODY OF IL7Rα AND USE THEREOF IN PREPARATION OF MEDICATION FOR TREATING TUMOR

(71) Applicant: Beijing Neurosurgical Institute, Beijing (CN)

(72) Inventors: Wei Zhang, Beijing (CN); Tao Jiang, Beijing (CN); You Zhai, Beijing (CN); Guanzhang Li, Beijing (CN)

(73) Assignee: Beijing Neurosurgical Institute, Beijing (CN)

( * ) Notice: Subject to any disclaimer, the term of this patent is extended or adjusted under 35 U.S.C. 154(b) by 845 days.

(21) Appl. No.: 18/019,010

(22) PCT Filed: Jul. 30, 2021

(86) PCT No.: PCT/CN2021/109864

§ 371 (c)(1),
(2) Date: Jan. 31, 2023

(87) PCT Pub. No.: WO2022/022719

PCT Pub. Date: Feb. 3, 2022

(65) Prior Publication Data

US 2024/0052014 A1 Feb. 15, 2024

(30) Foreign Application Priority Data

Jul. 31, 2020 (CN) ......................... 202010760960.3

(51) Int. Cl.

| | |
|---|---|
| ***C07K 14/715*** | (2006.01) |
| ***A61K 40/11*** | (2025.01) |
| ***A61K 40/31*** | (2025.01) |
| ***C07K 16/28*** | (2006.01) |
| ***C12N 15/63*** | (2006.01) |

(52) U.S. Cl.

CPC .......... *C07K 14/7155* (2013.01); *A61K 40/11* (2025.01); *A61K 40/31* (2025.01); *C07K 16/2884* (2013.01); *C07K 16/2896* (2013.01); *C12N 15/63* (2013.01); *A61K 2239/13* (2023.05); *C07K 2319/02* (2013.01); *C07K 2319/03* (2013.01)

(58) Field of Classification Search

CPC ............ C07K 14/7155; C07K 16/2884; C07K 16/2896; C07K 2319/02; C07K 2319/03; C07K 14/5418; C07K 2319/00; C07K 2317/622; A61K 40/11; A61K 40/31; A61K 2239/13; A61K 40/4202; A61K 40/4223; A61K 39/001119; A61K 2039/5158; C12N 15/63; C12N 2740/16043; C12N 15/62; C12N 15/86; C12N 5/0636; C12N 2510/00; C12N 2740/15043; A61P 35/00

See application file for complete search history.

(56) References Cited

U.S. PATENT DOCUMENTS

| | | | | |
|---|---|---|---|---|
| 2019/0359678 | A1 | 11/2019 | O'Donoghue et al. | |
| 2021/0000870 | A1 | 1/2021 | Jin et al. | |
| 2022/0387503 | A1* | 12/2022 | Kong | C07K 16/18 |

FOREIGN PATENT DOCUMENTS

| | | | | |
|---|---|---|---|---|
| CN | 107337737 | A | 11/2017 | |
| CN | 109503716 | A | 3/2019 | |
| CN | 110526987 | A | 12/2019 | |
| CN | 110564695 | A * | 12/2019 | A61K 39/001195 |
| CN | 110724200 | A | 1/2020 | |
| EP | 3 848 387 | A1 | 7/2021 | |
| WO | 2014/124143 | A1 | 8/2014 | |
| WO | 2017/029512 | A1 | 2/2017 | |
| WO | 2018/078066 | A1 | 5/2018 | |
| WO | 2019/055946 | A1 | 3/2019 | |
| WO | 2019/183094 | A1 | 9/2019 | |
| WO | WO-2020050667 | A1 * | 3/2020 | A61K 40/11 |
| WO | 2020/097582 | A1 | 5/2020 | |

OTHER PUBLICATIONS

Renaud-Gabardos et al. "Internal ribosome entry site-based vectors for combined gene therapy." 2015. World J Exp Med. 5(1): 11-20. (Year: 2015).*

Riet et al. "Nonviral RNA Transfection to Transiently Modify T Cells with Chimeric Antigen Receptors for Adoptive Therapy." 2012. Chapter 12, pp. 187-202. In: Rabinovich, P. (eds) Synthetic Messenger RNA and Cell Metabolism Modulation. Methods in Molecular Biology, vol. 969. Humana Press, Totowa, NJ (Year: 2012).*

Edwards et al. "The Remarkable Flexibility of the Human Antibody Repertoire; Isolation of Over One Thousand Different Antibodies to a Single Protein, BLyS." J. Mol. Biol., 2003, 334:103-118. (Year: 2003).*

Janeway Jr et al., "Structure of the Antibody Molecule and Immunoglobulin Genes." Immunology, 3rd Edition, 1997 Garland Publishing Inc., pp. 3:1-3:11. see entire selection (Year: 1997).*

Wang et al. "CD133-directed CAR T cells for advanced metastasis malignancies: A phase I trial." Oncoimmunology. 2018, 7(7); e1440169, 1-13 (Year: 2018).*

The extended European search report with the Supplementary European search report and the European search opinion, issued by the European Patent Office for European Patent Application No. 21849139.7, dated Sep. 18, 2024.

Perna et al., "Interleukin-7 Mediates Selective Expansion of Tumor-redirected Cytotoxic T Lymphocytes (CTLs) without Enhancement of Regulatory T-cell Inhibition", American Association for Cancer Research, Clinical Cancer Research, Jan. 2014, pp. 131-139, vol. 20, No. 1.

(Continued)

*Primary Examiner* — Misook Yu
*Assistant Examiner* — Grace H Lunde
(74) *Attorney, Agent, or Firm* — Myers Wolin, LLC

(57) ABSTRACT

The present disclosure relates to a truncated body of IL7Rα. The amino acid sequence of the truncated body of IL7Rα is a sequence shown in SEQ ID NO. 1. A T cell expressing a chimeric antigen receptor containing the truncated body of IL7Rα can effectively kill a tumor cell.

7 Claims, 3 Drawing Sheets

Specification includes a Sequence Listing.

(56) References Cited

OTHER PUBLICATIONS

International Search Report with the Written Opinion of the International Searching Authority issued by the China National Intellectual Property Administration for International Patent Application No. PCT/CN2021/109864, mailed on Oct. 8, 2021, with an English translation.

First Notification of Office Action and Search Report issued by the China National Intellectual Property Administration for Chinese Patent Application No. 2020107609603, dated Dec. 2, 2021, with an English translation.

* cited by examiner

SEQUENCE LISTING

```
<160> NUMBER OF SEQ ID NOS: 8

<210> SEQ ID NO 1
<211> LENGTH: 95
<212> TYPE: PRT
<213> ORGANISM: Artificial Sequence
<220> FEATURE:
<223> OTHER INFORMATION: This sequence is synthesized in lab.

<400> SEQUENCE: 1

Lys Lys Arg Ile Lys Pro Ile Val Trp Pro Ser Leu Pro Asp His Lys
1               5                   10                  15

Lys Thr Leu Glu His Leu Cys Lys Lys Pro Arg Lys Asn Leu Asn Val
            20                  25                  30

Ser Phe Asn Pro Glu Ser Phe Leu Asp Cys Gln Ile His Arg Val Asp
        35                  40                  45

Asp Ile Gln Ala Arg Asp Glu Val Glu Gly Phe Leu Gln Asp Thr Phe
    50                  55                  60

Pro Gln Gln Leu Glu Glu Ser Glu Lys Gln Arg Leu Leu Gly Ser Asn
65                  70                  75                  80

Gln Glu Glu Ala Tyr Val Thr Met Ser Ser Phe Tyr Gln Asn Gln
                85                  90                  95


<210> SEQ ID NO 2
<211> LENGTH: 285
<212> TYPE: DNA
<213> ORGANISM: Artificial Sequence
<220> FEATURE:
<223> OTHER INFORMATION: This sequence is synthesized in lab.

<400> SEQUENCE: 2

aaaaaaagga ttaagcctat cgtatggccc agtctccccg atcacaagaa gactctggaa     60
```

```
caccttgta agaaaccaag aaaaaattta aatgtgagtt tcaatcctga aagtttcctg    120

gactgccaga ttcatagggt ggatgacatt caagctagag atgaagtgga aggttttctg    180

caagatacgt ttcctcagca actagaagaa tctgagaagc agaggcttct gggatcaaat    240

caagaagaag catatgtcac catgtccagc ttctaccaaa accag                      285


<210> SEQ ID NO 3
<211> LENGTH: 822
<212> TYPE: PRT
<213> ORGANISM: Artificial Sequence
<220> FEATURE:
<223> OTHER INFORMATION: This sequence is synthesized in lab.

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Asp Tyr Arg Gly Tyr Tyr Gly Met Asp Val Trp Gly
            100                 105                 110

Gln Gly Thr Thr Val Thr Val Ser Ser Gly Ser Thr Ser Gly Gly Gly
        115                 120                 125

Ser Gly Gly Gly Ser Gly Gly Gly Gly Ser Ser Glu Ile Val Leu Thr
    130                 135                 140

Gln Ser Pro Ala Thr Leu Ser Leu Ser Pro Gly Glu Arg Ala Thr Leu
145                 150                 155                 160

Ser Cys Arg Ala Ser Gln Ser Val Ile Asn Tyr Leu Ala Trp Tyr Gln
                165                 170                 175

Gln Lys Pro Gly Gln Ala Pro Arg Leu Leu Ile Tyr Asp Ala Ser Asn
            180                 185                 190

Arg Ala Ser Gly Ile Pro Ala Arg Phe Ser Gly Ser Gly Ser Gly Thr
        195                 200                 205

Asp Phe Thr Leu Thr Ile Ser Ser Leu Glu Pro Glu Asp Phe Ala Val
    210                 215                 220

Tyr Tyr Cys Gln Gln Arg Arg Asn Trp Pro Leu Thr Phe Gly Gly Gly
225                 230                 235                 240

Thr Lys Val Glu Ile Lys Gly Gly Gly Gly Ser Gly Gly Gly Gly Ser
                245                 250                 255

Gly Gly Gly Gly Ser Gln Val Gln Leu Val Gln Ser Gly Ala Glu Val
            260                 265                 270

Lys Lys Pro Gly Ala Ser Val Lys Val Ser Cys Lys Ala Ser Gly Tyr
        275                 280                 285

Thr Phe Thr Asp Phe Glu Met His Trp Val Arg Gln Ala Pro Gly Gln
    290                 295                 300

Gly Leu Glu Trp Met Gly Asp Ile Asp Pro Gly Thr Gly Asp Thr Ala
305                 310                 315                 320
```

-continued

```
Tyr Asn Leu Lys Phe Lys Gly Arg Val Thr Met Thr Thr Asp Thr Ser
                325                 330                 335

Thr Ser Thr Ala Tyr Met Glu Leu Arg Ser Leu Arg Ser Asp Asp Thr
            340                 345                 350

Ala Val Tyr Tyr Cys Ala Leu Gly Ala Phe Val Tyr Trp Gly Gln Gly
        355                 360                 365

Thr Leu Val Thr Val Ser Ser Gly Ser Thr Ser Gly Gly Gly Ser Gly
    370                 375                 380

Gly Gly Ser Gly Gly Gly Gly Ser Ser Asp Val Val Met Thr Gln Ser
385                 390                 395                 400

Pro Leu Ser Leu Pro Val Thr Pro Gly Glu Pro Ala Ser Ile Ser Cys
                405                 410                 415

Arg Ser Ser Gln Ser Leu Ala Asn Ser Tyr Gly Asn Thr Tyr Leu Ser
            420                 425                 430

Trp Tyr Leu Gln Lys Pro Gly Gln Ser Pro Gln Leu Leu Ile Tyr Gly
        435                 440                 445

Ile Ser Asn Arg Phe Ser Gly Val Pro Asp Arg Phe Ser Gly Ser Gly
    450                 455                 460

Ser Gly Thr Asp Phe Thr Leu Lys Ile Ser Arg Val Glu Ala Glu Asp
465                 470                 475                 480

Val Gly Val Tyr Tyr Cys Leu Gln Gly Thr His Gln Pro Tyr Thr Phe
                485                 490                 495

Gly Gln Gly Thr Lys Leu Glu Ile Lys Thr Thr Thr Pro Ala Pro Arg
            500                 505                 510

Pro Pro Thr Pro Ala Pro Thr Ile Ala Ser Gln Pro Leu Ser Leu Arg
        515                 520                 525

Pro Glu Ala Cys Arg Pro Ala Ala Gly Gly Ala Val His Thr Arg Gly
    530                 535                 540

Leu Asp Phe Ala Cys Asp Ile Tyr Ile Trp Ala Pro Leu Ala Gly Thr
545                 550                 555                 560

Cys Gly Val Leu Leu Leu Ser Leu Val Ile Thr Leu Tyr Cys Arg Ser
                565                 570                 575

Lys Arg Ser Arg Leu Leu His Ser Asp Tyr Met Asn Met Thr Pro Arg
            580                 585                 590

Arg Pro Gly Pro Thr Arg Lys His Tyr Gln Pro Tyr Ala Pro Pro Arg
        595                 600                 605

Asp Phe Ala Ala Tyr Arg Ser Lys Lys Arg Ile Lys Pro Ile Val Trp
    610                 615                 620

Pro Ser Leu Pro Asp His Lys Lys Thr Leu Glu His Leu Cys Lys Lys
625                 630                 635                 640

Pro Arg Lys Asn Leu Asn Val Ser Phe Asn Pro Glu Ser Phe Leu Asp
                645                 650                 655

Cys Gln Ile His Arg Val Asp Asp Ile Gln Ala Arg Asp Glu Val Glu
            660                 665                 670

Gly Phe Leu Gln Asp Thr Phe Pro Gln Gln Leu Glu Glu Ser Glu Lys
        675                 680                 685

Gln Arg Leu Leu Gly Ser Asn Gln Glu Glu Ala Tyr Val Thr Met Ser
    690                 695                 700

Ser Phe Tyr Gln Asn Gln Arg Val Lys Phe Ser Arg Ser Ala Asp Ala
705                 710                 715                 720

Pro Ala Tyr Lys Gln Gly Gln Asn Gln Leu Tyr Asn Glu Leu Asn Leu
                725                 730                 735

Gly Arg Arg Glu Glu Tyr Asp Val Leu Asp Lys Arg Arg Gly Arg Asp
```

```
            740                 745                 750

Pro Glu Met Gly Gly Lys Pro Arg Arg Lys Asn Pro Gln Glu Gly Leu
        755                 760                 765

Tyr Asn Glu Leu Gln Lys Asp Lys Met Ala Glu Ala Tyr Ser Glu Ile
    770                 775                 780

Gly Met Lys Gly Glu Arg Arg Arg Gly Lys Gly His Asp Gly Leu Tyr
785                 790                 795                 800

Gln Gly Leu Ser Thr Ala Thr Lys Asp Thr Tyr Asp Ala Leu His Met
                805                 810                 815

Gln Ala Leu Pro Pro Arg
            820


<210> SEQ ID NO 4
<211> LENGTH: 2466
<212> TYPE: DNA
<213> ORGANISM: Artificial Sequence
<220> FEATURE:
<223> OTHER INFORMATION: This sequence is synthesized in lab.

<400> SEQUENCE: 4

caggtgcagc tggtggagtc tgggggaggc gtggtccagc ctgggaggtc cctgagactc     60

tcctgtgcag cgtctggatt caccttcagt agctatggca tgcactgggt ccgccaggct    120

ccaggcaagg ggctggagtg ggtggcagtt atatggtatg atggaagtaa taaattctat    180

gcagactccg tgaagggccg attcaccatc tccagagaca attccaagaa cacgctgtat    240

ctgcaaatga acagcctgag agccgaggac acggctgtgt attactgtgc gaggagaagt    300

gactacaggg gctactacgg tatggacgtc tggggccaag ggaccacggt caccgtctcc    360

tcaggcagta ctagcggtgg tggctccggg ggcggttccg gtgggggcgg cagcagcgaa    420

attgtgttga cacagtctcc agccaccctg tctttgtctc caggggaaag agccaccctc    480

tcctgcaggg ccagtcagag tgttatcaac tacttagcct ggtaccaaca gaaacctggc    540

caggctccca ggctcctcat ctatgatgca tccaacaggg cctctggcat cccagccagg    600

ttcagtggca gtgggtctgg gacagacttc actctcacca tcagcagcct agagcctgaa    660

gattttgcag tttattactg tcagcagcgt cgcaactggc cgctcacttt cggcggaggg    720

accaaggtgg agatcaaagg aggtggtgga tccggaggtg gtggctccgg aggtggtgga    780

tcccaggttc agctggtgca gtctggagct gaggtgaaga agcctggggc ctcagtgaag    840

gtctcctgca aggcttctgg ttacaccttt accgactttg aaatgcactg ggtgcgacag    900

gcccctggac aagggcttga gtggatggga gatattgatc ctggaactgg tgatactgcc    960

tacaatctga agttcaaggg cagagtcacc atgaccacag acacatccac gagcacagcc   1020

tacatggagc tgaggagcct gaggtctgac gacacggccg tgtattactg tgcgttgggg   1080

gcctttgttt actggggcca gggaaccctg gtcaccgtct cctcaggcag tactagcggt   1140

ggtggctccg gggcggttc cggtgggggc ggcagcagcg atgttgtgat gactcagtct   1200

ccactctccc tgcccgtcac ccctggagag ccggcctcca tctcctgcag gtctagtcag   1260

agtcttgcaa acagttatgg gaacacctat ttgtcttggt acctgcagaa gccagggcag   1320

tctccacagc tcctgatcta tgggatttcc aacagatttt ctggggtccc tgacaggttc   1380

agtggcagtg gatcaggcac agattttaca ctgaaaatca gcagagtgga ggctgaggac   1440

gttggggttt attactgctt acaaggtaca catcagccgt acacgtttgg ccaggggacc   1500

aagctggaga tcaaaaccac taccccagca ccgaggccac ccaccccggc tcctaccatc   1560
```

```
gcctcccagc ctctgtccct gcgtccggag gcatgtagac ccgcagctgg tggggccgtg   1620

catacccggg gtcttgactt cgcctgcgat atctacattt gggcccctct ggctggtact   1680

tgcggggtcc tgctgctttc actcgtgatc actctttact gtaggagtaa gaggagcagg   1740

ctcctgcaca gtgactacat gaacatgact ccccgccgcc ccgggcccac ccgcaagcat   1800

taccagccct atgccccacc acgcgacttc gcagcctatc gctccaaaaa aaggattaag   1860

cctatcgtat ggcccagtct ccccgatcac aagaagactc tggaacacct ttgtaagaaa   1920

ccaagaaaaa atttaaatgt gagtttcaat cctgaaagtt tcctggactg ccagattcat   1980

agggtggatg acattcaagc tagagatgaa gtggaaggtt ttctgcaaga tacgtttcct   2040

cagcaactag aagaatctga gaagcagagg cttctgggat caaatcaaga agaagcatat   2100

gtcaccatgt ccagcttcta ccaaaaccag cgcgtgaaat tcagccgcag cgcagatgct   2160

ccagcctaca agcaggggca gaaccagctc tacaacgaac tcaatcttgg tcggagagag   2220

gagtacgacg tgctggacaa gcggagagga cgggacccag aaatgggcgg gaagccgcgc   2280

agaaagaatc cccaagaggg cctgtacaac gagctccaaa aggataagat ggcagaagcc   2340

tatagcgaga ttggtatgaa aggggaacgc agaagaggca aaggccacga cggactgtac   2400

cagggactca gcaccgccac caaggacacc tatgacgctc ttcacatgca ggccctgccg   2460

cctcgg                                                              2466
```

```
<210> SEQ ID NO 5
<211> LENGTH: 2181
<212> TYPE: DNA
<213> ORGANISM: Artificial Sequence
<220> FEATURE:
<223> OTHER INFORMATION: This sequence is synthesized in lab.

<400> SEQUENCE: 5

caggtgcagc tggtggagtc tgggggaggc gtggtccagc ctgggaggtc cctgagactc     60

tcctgtgcag cgtctggatt caccttcagt agctatggca tgcactgggt ccgccaggct    120

ccaggcaagg ggctggagtg ggtggcagtt atatggtatg atggaagtaa taaattctat    180

gcagactccg tgaagggccg attcaccatc tccagagaca attccaagaa cacgctgtat    240

ctgcaaatga acagcctgag agccgaggac acggctgtgt attactgtgc gaggagaagt    300

gactacaggg gctactacgg tatggacgtc tggggccaag ggaccacggt caccgtctcc    360

tcaggcagta ctagcggtgg tggctccggg ggcggttccg gtgggggcgg cagcagcgaa    420

attgtgttga cacagtctcc agccaccctg tctttgtctc caggggaaag agccaccctc    480

tcctgcaggg ccagtcagag tgttatcaac tacttagcct ggtaccaaca gaaacctggc    540

caggctccca ggctcctcat ctatgatgca tccaacaggg cctctggcat cccagccagg    600

ttcagtggca gtgggtctgg gacagacttc actctcacca tcagcagcct agagcctgaa    660

gattttgcag tttattactg tcagcagcgt cgcaactggc cgctcacttt cggcggaggg    720

accaaggtgg agatcaaagg aggtggtgga tccggaggtg gtggctccgg aggtggtgga    780

tcccaggttc agctggtgca gtctggagct gaggtgaaga agcctggggc ctcagtgaag    840

gtctcctgca aggcttctgg ttacaccttt accgactttg aaatgcactg ggtgcgacag    900

gcccctggac aagggcttga gtggatggga gatattgatc ctggaactgg tgatactgcc    960

tacaatctga agttcaaggg cagagtcacc atgaccacag acacatccac gagcacagcc   1020

tacatggagc tgaggagcct gaggtctgac gacacggccg tgtattactg tgcgttgggg   1080

gcctttgttt actggggcca gggaaccctg gtcaccgtct cctcaggcag tactagcggt   1140
```

```
ggtggctccg gggcggttc cggtgggggc ggcagcagcg atgttgtgat gactcagtct   1200
ccactctccc tgcccgtcac ccctggagag ccggcctcca tctcctgcag gtctagtcag   1260
agtcttgcaa acagttatgg gaacacctat ttgtcttggt acctgcagaa gccagggcag   1320
tctccacagc tcctgatcta tgggatttcc aacagatttt ctggggtccc tgacaggttc   1380
agtggcagtg gatcaggcac agattttaca ctgaaaatca gcagagtgga ggctgaggac   1440
gttggggttt attactgctt acaaggtaca catcagccgt acacgtttgg ccaggggacc   1500
aagctggaga tcaaaaccac taccccagca ccgaggccac ccaccccggc tcctaccatc   1560
gcctcccagc ctctgtccct gcgtccggag gcatgtagac ccgcagctgg tggggccgtg   1620
catacccggg gtcttgactt cgcctgcgat atctacattt gggcccctct ggctggtact   1680
tgcggggtcc tgctgctttc actcgtgatc actctttact gtaggagtaa gaggagcagg   1740
ctcctgcaca gtgactacat gaacatgact ccccgccgcc ccgggcccac ccgcaagcat   1800
taccagccct atgccccacc acgcgacttc gcagcctatc gctcccgcgt gaaattcagc   1860
cgcagcgcag atgctccagc ctacaagcag gggcagaacc agctctacaa cgaactcaat   1920
cttggtcgga gagaggagta cgacgtgctg gacaagcgga gaggacggga cccagaaatg   1980
ggcgggaagc cgcgcagaaa gaatccccaa gagggcctgt acaacgagct ccaaaaggat   2040
aagatggcag aagcctatag cgagattggt atgaaagggg aacgcagaag aggcaaaggc   2100
cacgacggac tgtaccaggg actcagcacc gccaccaagg acacctatga cgctcttcac   2160
atgcaggccc tgccgcctcg g                                              2181
```

<210> SEQ ID NO 6
<211> LENGTH: 2766
<212> TYPE: DNA
<213> ORGANISM: Artificial Sequence
<220> FEATURE:
<223> OTHER INFORMATION: This sequence is synthesized in lab.

<400> SEQUENCE: 6

```
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtatg atggaagtaa taaattctat    180
gcagactccg tgaagggccg attcaccatc tccagagaca attccaagaa cacgctgtat    240
ctgcaaatga acagcctgag agccgaggac acggctgtgt attactgtgc gaggagaagt    300
gactacaggg gctactacgg tatggacgtc tggggccaag ggaccacggt caccgtctcc    360
tcaggcagta ctagcggtgg tggctccggg ggcggttccg gtgggggcgg cagcagcgaa    420
attgtgttga cacagtctcc agccaccctg tctttgtctc caggggaaag agccaccctc    480
tcctgcaggg ccagtcagag tgttatcaac tacttagcct ggtaccaaca gaaacctggc    540
caggctccca ggctcctcat ctatgatgca tccaacaggg cctctggcat cccagccagg    600
ttcagtggca gtgggtctgg gacagacttc actctcacca tcagcagcct agagcctgaa    660
gattttgcag tttattactg tcagcagcgt cgcaactggc cgctcacttt cggcggaggg    720
accaaggtgg agatcaaagg aggtggtgga tccggaggtg gtggctccgg aggtggtgga    780
tcccaggttc agctggtgca gtctggagct gaggtgaaga agcctggggc ctcagtgaag    840
gtctcctgca aggcttctgg ttacaccttt accgactttg aaatgcactg ggtgcgacag    900
gcccctggac aagggcttga gtggatggga gatattgatc ctggaactgg tgatactgcc    960
```

-continued

```
tacaatctga agttcaaggg cagagtcacc atgaccacag acacatccac gagcacagcc   1020

tacatggagc tgaggagcct gaggtctgac gacacggccg tgtattactg tgcgttgggg   1080

gcctttgttt actggggcca gggaaccctg gtcaccgtct cctcaggcag tactagcggt   1140

ggtggctccg gggcggttc cggtgggggc ggcagcagcg atgttgtgat gactcagtct   1200

ccactctccc tgcccgtcac ccctggagag ccggcctcca tctcctgcag gtctagtcag   1260

agtcttgcaa acagttatgg gaacacctat ttgtcttggt acctgcagaa gccagggcag   1320

tctccacagc tcctgatcta tgggatttcc aacagatttt ctggggtccc tgacaggttc   1380

agtggcagtg gatcaggcac agattttaca ctgaaaatca gcagagtgga ggctgaggac   1440

gttggggttt attactgctt acaaggtaca catcagccgt acacgtttgg ccaggggacc   1500

aagctggaga tcaaaaccac taccccagca ccgaggccac ccaccccggc tcctaccatc   1560

gcctcccagc ctctgtccct gcgtccggag gcatgtagac ccgcagctgg tggggccgtg   1620

catacccggg gtcttgactt cgcctgcgat atctacattt gggcccctct ggctggtact   1680

tgcggggtcc tgctgctttc actcgtgatc actctttact gtaggagtaa gaggagcagg   1740

ctcctgcaca gtgactacat gaacatgact ccccgccgcc ccgggcccac ccgcaagcat   1800

taccagccct atgccccacc acgcgacttc gcagcctatc gctccaaaaa aaggattaag   1860

cctatcgtat ggcccagtct ccccgatcat aagaagactc tggaacatct ttgtaagaaa   1920

ccaagaaaaa atttaaatgt gagtttcaat cctgaaagtt tcctggactg ccagattcat   1980

agggtggatg acattcaagc tagagatgaa gtggaaggtt ttctgcaaga tacgtttcct   2040

cagcaactag aagaatctga gaagcagagg cttggagggg atgtgcagag ccccaactgc   2100

ccatctgagg atgtagtcat cactccagaa agctttggaa gagattcatc cctcacatgc   2160

ctggctggga atgtcagtgc atgtgacgcc cctattctct cccttccag gtccctagac   2220

tgcagggaga gtggcaagaa tggcctcat gtgtaccagg acctcctgct tagccttggg   2280

actacaaaca gcacgctgcc ccctccattt tctctccaat ctggaatcct gacattgaac   2340

ccagttgctc agggtcagcc cattcttact tccctgggat caaatcaaga agaagcatat   2400

gtcaccatgt ccagcttcta ccaaaaccag cgcgtgaaat tcagccgcag cgcagatgct   2460

ccagcctaca agcaggggca gaaccagctc tacaacgaac tcaatcttgg tcggagagag   2520

gagtacgacg tgctggacaa gcggagagga cgggacccag aaatgggcgg gaagccgcgc   2580

agaaagaatc cccaagaggg cctgtacaac gagctccaaa aggataagat ggcagaagcc   2640

tatagcgaga ttggtatgaa aggggaacgc agaagaggca aaggccacga cggactgtac   2700

cagggactca gcaccgccac caaggacacc tatgacgctc ttcacatgca ggccctgccg   2760

cctcgg                                                              2766
```

<210> SEQ ID NO 7
<211> LENGTH: 727
<212> TYPE: PRT
<213> ORGANISM: Artificial Sequence
<220> FEATURE:
<223> OTHER INFORMATION: This sequence is synthesized in lab.

<400> SEQUENCE: 7

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
```

-continued

```
        35                  40                  45

Ala Val Ile Trp Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Asp Tyr Arg Gly Tyr Tyr Gly Met Asp Val Trp Gly
            100                 105                 110

Gln Gly Thr Thr Val Thr Val Ser Ser Gly Ser Thr Ser Gly Gly Gly
        115                 120                 125

Ser Gly Gly Gly Ser Gly Gly Gly Gly Ser Ser Glu Ile Val Leu Thr
    130                 135                 140

Gln Ser Pro Ala Thr Leu Ser Leu Ser Pro Gly Glu Arg Ala Thr Leu
145                 150                 155                 160

Ser Cys Arg Ala Ser Gln Ser Val Ile Asn Tyr Leu Ala Trp Tyr Gln
                165                 170                 175

Gln Lys Pro Gly Gln Ala Pro Arg Leu Leu Ile Tyr Asp Ala Ser Asn
            180                 185                 190

Arg Ala Ser Gly Ile Pro Ala Arg Phe Ser Gly Ser Gly Ser Gly Thr
        195                 200                 205

Asp Phe Thr Leu Thr Ile Ser Ser Leu Glu Pro Glu Asp Phe Ala Val
    210                 215                 220

Tyr Tyr Cys Gln Gln Arg Arg Asn Trp Pro Leu Thr Phe Gly Gly Gly
225                 230                 235                 240

Thr Lys Val Glu Ile Lys Gly Gly Gly Gly Ser Gly Gly Gly Gly Ser
                245                 250                 255

Gly Gly Gly Gly Ser Gln Val Gln Leu Val Gln Ser Gly Ala Glu Val
            260                 265                 270

Lys Lys Pro Gly Ala Ser Val Lys Val Ser Cys Lys Ala Ser Gly Tyr
        275                 280                 285

Thr Phe Thr Asp Phe Glu Met His Trp Val Arg Gln Ala Pro Gly Gln
    290                 295                 300

Gly Leu Glu Trp Met Gly Asp Ile Asp Pro Gly Thr Gly Asp Thr Ala
305                 310                 315                 320

Tyr Asn Leu Lys Phe Lys Gly Arg Val Thr Met Thr Thr Asp Thr Ser
                325                 330                 335

Thr Ser Thr Ala Tyr Met Glu Leu Arg Ser Leu Arg Ser Asp Asp Thr
            340                 345                 350

Ala Val Tyr Tyr Cys Ala Leu Gly Ala Phe Val Tyr Trp Gly Gln Gly
        355                 360                 365

Thr Leu Val Thr Val Ser Ser Gly Ser Thr Ser Gly Gly Gly Ser Gly
    370                 375                 380

Gly Gly Ser Gly Gly Gly Gly Ser Ser Asp Val Val Met Thr Gln Ser
385                 390                 395                 400

Pro Leu Ser Leu Pro Val Thr Pro Gly Glu Pro Ala Ser Ile Ser Cys
                405                 410                 415

Arg Ser Ser Gln Ser Leu Ala Asn Ser Tyr Gly Asn Thr Tyr Leu Ser
            420                 425                 430

Trp Tyr Leu Gln Lys Pro Gly Gln Ser Pro Gln Leu Leu Ile Tyr Gly
        435                 440                 445

Ile Ser Asn Arg Phe Ser Gly Val Pro Asp Arg Phe Ser Gly Ser Gly
    450                 455                 460
```

```
Ser Gly Thr Asp Phe Thr Leu Lys Ile Ser Arg Val Glu Ala Glu Asp
465                 470                 475                 480

Val Gly Val Tyr Tyr Cys Leu Gln Gly Thr His Gln Pro Tyr Thr Phe
                485                 490                 495

Gly Gln Gly Thr Lys Leu Glu Ile Lys Thr Thr Thr Pro Ala Pro Arg
            500                 505                 510

Pro Pro Thr Pro Ala Pro Thr Ile Ala Ser Gln Pro Leu Ser Leu Arg
        515                 520                 525

Pro Glu Ala Cys Arg Pro Ala Ala Gly Gly Ala Val His Thr Arg Gly
    530                 535                 540

Leu Asp Phe Ala Cys Asp Ile Tyr Ile Trp Ala Pro Leu Ala Gly Thr
545                 550                 555                 560

Cys Gly Val Leu Leu Leu Ser Leu Val Ile Thr Leu Tyr Cys Arg Ser
                565                 570                 575

Lys Arg Ser Arg Leu Leu His Ser Asp Tyr Met Asn Met Thr Pro Arg
            580                 585                 590

Arg Pro Gly Pro Thr Arg Lys His Tyr Gln Pro Tyr Ala Pro Pro Arg
        595                 600                 605

Asp Phe Ala Ala Tyr Arg Ser Arg Val Lys Phe Ser Arg Ser Ala Asp
    610                 615                 620

Ala Pro Ala Tyr Lys Gln Gly Gln Asn Gln Leu Tyr Asn Glu Leu Asn
625                 630                 635                 640

Leu Gly Arg Arg Glu Glu Tyr Asp Val Leu Asp Lys Arg Arg Gly Arg
                645                 650                 655

Asp Pro Glu Met Gly Gly Lys Pro Arg Arg Lys Asn Pro Gln Glu Gly
            660                 665                 670

Leu Tyr Asn Glu Leu Gln Lys Asp Lys Met Ala Glu Ala Tyr Ser Glu
        675                 680                 685

Ile Gly Met Lys Gly Glu Arg Arg Arg Gly Lys Gly His Asp Gly Leu
    690                 695                 700

Tyr Gln Gly Leu Ser Thr Ala Thr Lys Asp Thr Tyr Asp Ala Leu His
705                 710                 715                 720

Met Gln Ala Leu Pro Pro Arg
                725


<210> SEQ ID NO 8
<211> LENGTH: 921
<212> TYPE: PRT
<213> ORGANISM: Artificial Sequence
<220> FEATURE:
<223> OTHER INFORMATION: This sequence is synthesized in lab.

<400> SEQUENCE: 8

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Arg Ser Asp Tyr Arg Gly Tyr Tyr Gly Met Asp Val Trp Gly
            100                 105                 110

Gln Gly Thr Thr Val Thr Val Ser Ser Gly Ser Thr Ser Gly Gly Gly
        115                 120                 125

Ser Gly Gly Gly Ser Gly Gly Gly Gly Ser Ser Glu Ile Val Leu Thr
    130                 135                 140

Gln Ser Pro Ala Thr Leu Ser Leu Ser Pro Gly Glu Arg Ala Thr Leu
145                 150                 155                 160

Ser Cys Arg Ala Ser Gln Ser Val Ile Asn Tyr Leu Ala Trp Tyr Gln
                165                 170                 175

Gln Lys Pro Gly Gln Ala Pro Arg Leu Leu Ile Tyr Asp Ala Ser Asn
            180                 185                 190

Arg Ala Ser Gly Ile Pro Ala Arg Phe Ser Gly Ser Gly Ser Gly Thr
        195                 200                 205

Asp Phe Thr Leu Thr Ile Ser Ser Leu Glu Pro Glu Asp Phe Ala Val
    210                 215                 220

Tyr Tyr Cys Gln Gln Arg Arg Asn Trp Pro Leu Thr Phe Gly Gly Gly
225                 230                 235                 240

Thr Lys Val Glu Ile Lys Gly Gly Gly Gly Ser Gly Gly Gly Gly Ser
                245                 250                 255

Gly Gly Gly Gly Ser Gln Val Gln Leu Val Gln Ser Gly Ala Glu Val
            260                 265                 270

Lys Lys Pro Gly Ala Ser Val Lys Val Ser Cys Lys Ala Ser Gly Tyr
        275                 280                 285

Thr Phe Thr Asp Phe Glu Met His Trp Val Arg Gln Ala Pro Gly Gln
    290                 295                 300

Gly Leu Glu Trp Met Gly Asp Ile Asp Pro Gly Thr Gly Asp Thr Ala
305                 310                 315                 320

Tyr Asn Leu Lys Phe Lys Gly Arg Val Thr Met Thr Thr Asp Thr Ser
                325                 330                 335

Thr Ser Thr Ala Tyr Met Glu Leu Arg Ser Leu Arg Ser Asp Asp Thr
            340                 345                 350

Ala Val Tyr Tyr Cys Ala Leu Gly Ala Phe Val Tyr Trp Gly Gln Gly
        355                 360                 365

Thr Leu Val Thr Val Ser Ser Gly Ser Thr Ser Gly Gly Gly Ser Gly
    370                 375                 380

Gly Gly Ser Gly Gly Gly Gly Ser Ser Asp Val Val Met Thr Gln Ser
385                 390                 395                 400

Pro Leu Ser Leu Pro Val Thr Pro Gly Glu Pro Ala Ser Ile Ser Cys
                405                 410                 415

Arg Ser Ser Gln Ser Leu Ala Asn Ser Tyr Gly Asn Thr Tyr Leu Ser
            420                 425                 430

Trp Tyr Leu Gln Lys Pro Gly Gln Ser Pro Gln Leu Leu Ile Tyr Gly
        435                 440                 445

Ile Ser Asn Arg Phe Ser Gly Val Pro Asp Arg Phe Ser Gly Ser Gly
    450                 455                 460

Ser Gly Thr Asp Phe Thr Leu Lys Ile Ser Arg Val Glu Ala Glu Asp
465                 470                 475                 480

Val Gly Val Tyr Tyr Cys Leu Gln Gly Thr His Gln Pro Tyr Thr Phe
                485                 490                 495

Gly Gln Gly Thr Lys Leu Glu Ile Lys Thr Thr Thr Pro Ala Pro Arg
            500                 505                 510
```

-continued

```
Pro Pro Thr Pro Ala Pro Thr Ile Ala Ser Gln Pro Leu Ser Leu Arg
        515                 520                 525

Pro Glu Ala Cys Arg Pro Ala Ala Gly Gly Ala Val His Thr Arg Gly
    530                 535                 540

Leu Asp Phe Ala Cys Asp Ile Tyr Ile Trp Ala Pro Leu Ala Gly Thr
545                 550                 555                 560

Cys Gly Val Leu Leu Leu Ser Leu Val Ile Thr Leu Tyr Cys Arg Ser
                565                 570                 575

Lys Arg Ser Arg Leu Leu His Ser Asp Tyr Met Asn Met Thr Pro Arg
            580                 585                 590

Arg Pro Gly Pro Thr Arg Lys His Tyr Gln Pro Tyr Ala Pro Pro Arg
        595                 600                 605

Asp Phe Ala Ala Tyr Arg Ser Lys Lys Arg Ile Lys Pro Ile Val Trp
    610                 615                 620

Pro Ser Leu Pro Asp His Lys Lys Thr Leu Glu His Leu Cys Lys Lys
625                 630                 635                 640

Pro Arg Lys Asn Leu Asn Val Ser Phe Asn Pro Glu Ser Phe Leu Asp
                645                 650                 655

Cys Gln Ile His Arg Val Asp Asp Ile Gln Ala Arg Asp Glu Val Glu
            660                 665                 670

Gly Phe Leu Gln Asp Thr Phe Pro Gln Gln Leu Glu Glu Ser Glu Lys
        675                 680                 685

Gln Arg Leu Gly Gly Asp Val Gln Ser Pro Asn Cys Pro Ser Glu Asp
    690                 695                 700

Val Val Ile Thr Pro Glu Ser Phe Gly Arg Asp Ser Ser Leu Thr Cys
705                 710                 715                 720

Leu Ala Gly Asn Val Ser Ala Cys Asp Ala Pro Ile Leu Ser Pro Ser
                725                 730                 735

Arg Ser Leu Asp Cys Arg Glu Ser Gly Lys Asn Gly Pro His Val Tyr
            740                 745                 750

Gln Asp Leu Leu Leu Ser Leu Gly Thr Thr Asn Ser Thr Leu Pro Pro
        755                 760                 765

Pro Phe Ser Leu Gln Ser Gly Ile Leu Thr Leu Asn Pro Val Ala Gln
    770                 775                 780

Gly Gln Pro Ile Leu Thr Ser Leu Gly Ser Asn Gln Glu Glu Ala Tyr
785                 790                 795                 800

Val Thr Met Ser Ser Phe Tyr Gln Asn Gln Arg Val Lys Phe Ser Arg
                805                 810                 815

Ser Ala Asp Ala Pro Ala Tyr Lys Gln Gly Gln Asn Gln Leu Tyr Asn
            820                 825                 830

Glu Leu Asn Leu Gly Arg Arg Glu Glu Tyr Asp Val Leu Asp Lys Arg
        835                 840                 845

Arg Gly Arg Asp Pro Glu Met Gly Gly Lys Pro Arg Lys Asn Pro Gln
    850                 855                 860

Glu Gly Leu Tyr Asn Glu Leu Gln Lys Asp Lys Met Ala Glu Ala Tyr
865                 870                 875                 880

Ser Glu Ile Gly Met Lys Gly Glu Arg Arg Arg Gly Lys Gly His Asp
                885                 890                 895

Gly Leu Tyr Gln Gly Leu Ser Thr Ala Thr Lys Asp Thr Tyr Asp Ala
            900                 905                 910

Leu His Met Gln Ala Leu Pro Pro Arg
        915                 920
```

TRUNCATED BODY OF IL7Rα AND USE THEREOF IN PREPARATION OF MEDICATION FOR TREATING TUMOR

CROSS-REFERENCE TO RELATED APPLICATION

This application is a national stage application under 35 U.S.C. 371 of International Application No. PCT/CN2021/109864, filed on Jul. 30, 2021, which claims priority to Chinese Patent Application No. 202010760960.3, filed on Jul. 31, 2020, the entire contents of each are herein wholly incorporated by reference.

The material in the ASCII text file report (inno_13455_20230209_sequence_listing_rev.txt; and Date of Creation: Feb. 9, 2023, having the size of 33,381 bytes, filed for the present application via EFS-web in replacement of electronic sequence listing (inno_13145_20230131_Sequence_listing.txt; Size: 33,382 bytes; and Date of Creation: Jan. 31, 2023), is incorporated by reference in the specification for all purposes. The Sequence listing includes no new matter.

TECHNICAL FIELD

The disclosure relates to the field of pharmaceutical biotechnology, in particular to a truncated body of IL7Rα, an encoding nucleic acid, an expression vector, a cell, a pharmaceutical composition and use thereof.

BACKGROUND

Chimeric antigen receptor (CAR) is a synthetic T cell receptor consisting of an antigen binding domain, a transmembrane domain and an intracellular signaling domain. The antigen binding domain is located outside a T cell membrane, includes a single-chain antibody or ligand, and is used for specifically binding to a target antigen. The intracellular signaling domain is located in the T cell membrane, and is used for transmitting signals to a T cell to stimulate the immune response of the T cell.

The CAR can target and identify the target antigen on the surface of a tumor cell, so the T cell expressing the CAR can be used for targeting and killing a tumor cell. However, the existing T cell expressing the CAR is still weak in killing the tumor cell.

SUMMARY

The objective of the disclosure is to overcome the problem that the existing T cell expressing a chimeric antigen receptor (CAR) is still weak in killing a tumor cell, and to provide a truncated body of IL7Rα.

In order to achieve the above objective, in a first aspect, the disclosure provides a truncated body of IL7Rα, the amino acid sequence of which includes a sequence shown in SEQ ID NO. 1.

In a second aspect, the disclosure provides a nucleic acid encoding the truncated body of IL7Rα according to the first aspect; and preferably, the nucleic acid has a nucleotide sequence shown in SEQ ID NO. 2.

In a third aspect, the disclosure provides a fusion protein containing an antigen binding domain, a transmembrane domain and an intracellular signaling domain that are sequentially linked; the amino acid sequence of the intracellular signaling domain includes the amino acid sequence of the truncated body of IL7Rα according to the first aspect; preferably, the antigen binding domain includes an anti-CD44 single-chain antibody and/or an anti-CD133 single-chain antibody, and the intracellular signaling domain includes the truncated body of IL7Rα; and more preferably, the fusion protein has an amino acid sequence shown in SEQ ID NO. 3.

In a fourth aspect, the disclosure provides a fusion nucleic acid encoding the fusion protein according to the third aspect; and preferably, the fusion nucleic acid has a nucleotide sequence shown in SEQ ID NO. 4.

In a fifth aspect, the disclosure provides an expression vector, the expression vector is inserted with an expression cassette, the expression cassette includes a first nucleic acid fragment encoding an antigen binding molecule and a second nucleic acid fragment encoding an intracellular signaling molecule, the intracellular signaling molecule contains the truncated body of IL7Rα according to the first aspect, and an IRES element or a 2 A peptide encoding sequence is inserted between the first nucleic acid fragment and the second nucleic acid fragment; and preferably, the expression cassette is the fusion nucleic acid according to the fourth aspect.

In a sixth aspect, the disclosure provides a cell expressing a chimeric antigen receptor, the cell expressing a chimeric antigen receptor is obtained by transfection of the expression vector according to the fifth aspect by a host cell, and the chimeric antigen receptor contains the truncated body of IL7Rα according to the first aspect.

Optionally, the host cell is a T cell.

In a seventh aspect, the disclosure provides use of the truncated body of IL7Rα according to the first aspect, the nucleic acid according to the second aspect, the fusion protein according to the third aspect, the fusion nucleic acid according to the fourth aspect, the expression vector according to the fifth aspect, and the cell expressing a chimeric antigen receptor according to the sixth aspect in preparation of a medication for treating a tumor.

Optionally, the tumor is glioma.

In an eighth aspect, the disclosure provides a pharmaceutical composition, an active ingredient of which includes the cell expressing a chimeric antigen receptor containing the truncated body of IL7Rα according to the sixth aspect.

Through the above technical solution, a T cell expressing a chimeric antigen receptor containing the truncated body of IL7Rα provided by the disclosure can effectively kill a tumor cell.

Other features and advantages of the disclosure will be described in detail in the following specific embodiments.

BRIEF DESCRIPTION OF THE DRAWINGS

The accompanying drawings are intended to provide a further understanding of the disclosure, constitute a part of the description, and are used for interpreting the disclosure together with the following specific embodiments, rather than limiting the disclosure. In the figures.

DETAILED DESCRIPTION

Figure 1:
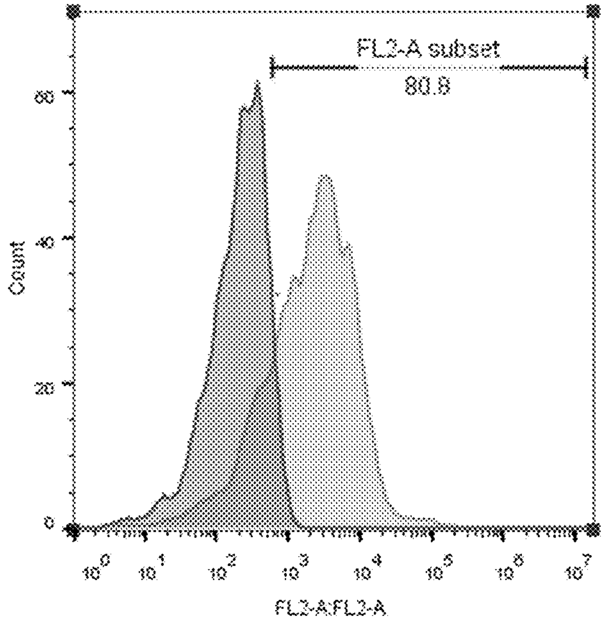
FIG. 1 is a flow cytometer test result diagram of CAR-T 1 cells according to an embodiment of the disclosure.

The specific embodiments of the disclosure will be described in detail below with reference to the accompanying drawings. It should be understood that the specific embodiments described herein are merely used for illustrating and interpreting the disclosure, rather than limiting the disclosure.

A first aspect of the disclosure provides a truncated body of IL7Rα. The amino acid sequence of the truncated body of IL7Rα includes a sequence shown in SEQ ID NO. 1.

The sequence shown in SEQ ID NO. 1 is as follows:

KKRIKPIVWPSLPDHKKTLEHLCKKPRKNLNVSFNPESFLDCQIHRVDD

IQARDEVEGFLQDTFPQQLEESEKQRLLGSNQEEAYVTMSSFYQNQ.

The inventors of the disclosure found that the above-mentioned truncated body of IL7Rα can effectively prolong the survival time of an activated T cell. Therefore, a T cell expressing a chimeric antigen receptor containing the truncated body of IL7Rα has a long survival time and can effectively kill a tumor cell.

A second aspect of the disclosure provides a nucleic acid encoding the truncated body of IL7Rα according to the first aspect. Preferably, the nucleic acid has a nucleotide sequence shown in SEQ ID NO. 2.

The nucleotide sequence shown in SEQ ID NO. 2 is as follows:

aaaaaaaggattaagcctatcgtatggcccagtctccccgatcacaaga agactctggaacacctttgtaagaaaccaagaaaaaatttaaatgtgag tttcaatcctgaaagtttcctggactgccagattcatagggtggatgac attcaagctagagatgaagtggaaggttttctgcaagatacgtttcctc agcaactagaagaatctgagaagcagaggcttctgggatcaaatcaaga agaagcatatgtcaccatgtccagcttctaccaaaaccag.

A third aspect of the disclosure provides a fusion protein containing an antigen binding domain, a transmembrane domain and an intracellular signaling domain that are sequentially linked. The amino acid sequence of the intracellular signaling domain includes the amino acid sequence of the truncated body of IL7Rα according to the first aspect. Preferably, the antigen binding domain includes an anti-CD44 single-chain antibody and/or an anti-CD133 single-chain antibody, and the intracellular signaling domain includes the truncated body of IL7Rα. More preferably, the fusion protein has an amino acid sequence shown in SEQ ID NO. 3.

The fusion protein shown in SEQ ID NO. 3 consists of an anti-CD44 single-chain antibody, an anti-CD133 single-chain antibody, a CD28, a truncated body of IL7Rα, and a CD3.

The amino acid sequence shown in SEQ ID NO. 3 is as follows:

QVQLVESGGGVVQPGRSLRLSCAASGFTFSSYGMHWVRQAPGKGLEWVA

VIWYDGSNKFYADSVKGRFTISRDNSKNTLYLQMNSLRAEDTAVYYCAR

RSDYRGYYGMDVWGQGTTVTVSSGSTSGGGSGGGSGGGGSSEIVLTQSP

ATLSLSPGERATLSCRASQSVINYLAWYQQKPGQAPRLLIYDASNRASG

IPARFSGSGSGTDFTLTISSLEPEDFAVYYCQQRRNWPLTFGGGTKVEI

KGGGGSGGGGSGGGGSQVQLVQSGAEVKKPGASVKVSCKASGYTFTDFE

MHWVRQAPGQGLEWMGDIDPGTGDTAYNLKFKGRVTMTTDTSTSTAYME

LRSLRSDDTAVYYCALGAFVYWGQGTLVTVSSGSTSGGGSGGGSGGGGS

SDVVMTQSPLSLPVTPGEPASISCRSSQSLANSYGNTYLSWYLQKPGQS

PQLLIYGISNRFSGVPDRFSGSGSGTDFTLKISRVEAEDVGVYYCLQGT

HQPYTFGQGTKLEIKTTTPAPRPPTPAPTIASQPLSLRPEACRPAAGGA

VHTRGLDFACDIYIWAPLAGTCGVLLLSLVITLYCRSKRSRLLHSDYMN

MTPRRPGPTRKHYQPYAPPRDFAAYRSKKRIKPIVWPSLPDHKKTLEHL

CKKPRKNLNVSFNPESFLDCQIHRVDDIQARDEVEGFLQDTFPQQLEES

EKQRLLGSNQEEAYVTMSSFYQNQRVKFSRSADAPAYKQGQNQLYNELN

LGRREEYDVLDKRRGRDPEMGGKPRRKNPQEGLYNELQKDKMAEAYSEI

GMKGERRRGKGHDGLYQGLSTATKDTYDALHMQALPPR.

A fourth aspect of the disclosure provides a fusion nucleic acid encoding the fusion protein according to the third aspect. Preferably, the fusion nucleic acid has a nucleotide sequence shown in SEQ ID NO. 4.

The nucleotide sequence shown in SEQ ID NO. 4 is used for encoding the amino acid sequence shown in SEQ ID NO. 3.

The nucleotide sequence shown in SEQ ID NO. 4 is as follows:

caggtgcagctggtggagtctgggggaggcgtggtccagcctgggaggtccctgagactctcctgtgcagcgtctggattc accttcagtagctatggcatgcactgggtccgccaggctccaggcaaggggctggagtgggtggcagttatatggtatgatggaagtaat aaattctatgcagactccgtgaagggccgattcaccatctccagagacaattccaagaacacgctgtatctgcaaatgaacagcctgagag ccgaggacacggctgtgtattactgtgcgaggagaagtgactacaggggctactacggtatggacgtctggggccaagggaccacggt caccgtctcctcaggcagtactagcggtggtggctccgggggcggttccggtgggggcggcagcagcgaaattgtgttgacacagtctc cagccaccctgtctttgtctccaggggaaagagccaccctctcctgcagggccagtcagagtgttatcaactacttagcctggtaccaaca gaaacctggccaggctcccaggctcctcatctatgatgcatccaacagggcctctggcatcccagccaggttcagtggcagtgggtctgg gacagacttcactctcaccatcagcagcctagagcctgaagattttgcagtttattactgtcagcagcgtcgcaactggccgctcactttcgg cggagggaccaaggtggagatcaaaggaggtggtggatccggaggtggtggctccggaggtggtggatcccaggttcagctggtgca gtctggagctgaggtgaagaagcctggggcctcagtgaaggtctcctgcaaggcttctggttacacctttaccgactttgaaatgcactggg tgcgacaggcccctggacaagggcttgagtggatgggagatattgatcctggaactggtgatactgcctacaatctgaagttcaagggca -continued

```
gagtcaccatgaccacagacacatccacgagcacagcctacatggagctgaggagcctgaggtctgacgacacggccgtgtattactgt

gcgttgggggcctttgtttactggggccagggaaccctggtcaccgtctcctcaggcagtactagcggtggtggctccgggggcggttcc

ggtgggggcggcagcagcgatgttgtgatgactcagtctccactctccctgcccgtcacccctggagagccggcctccatctcctgcagg

tctagtcagagtcttgcaaacagttatgggaacacctatttgtcttggtacctgcagaagccagggcagtctccacagctcctgatctatggg

atttccaacagattttctggggtccctgacaggttcagtggcagtggatcaggcacagattttacactgaaaatcagcagagtggaggctga

ggacgttggggtttattactgcttacaaggtacacatcagccgtacacgtttggccaggggaccaagctggagatcaaaaccactacccca

gcaccgaggccacccaccccggctcctaccatcgcctcccagcctctgtccctgcgtccggaggcatgtagacccgcagctggtgggg

ccgtgcatacccggggtcttgacttcgcctgcgatatctacatttgggcccctctggctggtacttgcggggtcctgctgctttcactcgtgat

cactctttactgtaggagtaagaggagcaggctcctgcacagtgactacatgaacatgactccccgccgccccgggcccacccgcaagc

attaccagccctatgccccaccacgcgacttcgcagcctatcgctccaaaaaaaggattaagcctatcgtatggcccagtctccccgatca

caagaagactctggaacacctttgtaagaaaccaagaaaaatttaaatgtgagtttcaatcctgaaagtttcctggactgccagattcatag

ggtggatgacattcaagctagagatgaagtggaaggttttctgcaagatacgtttcctcagcaactagaagaatctgagaagcagaggcttc

tgggatcaaatcaagaagaagcatatgtcaccatgtccagcttctaccaaaaccagcgcgtgaaattcagccgcagcgcagatgctccag

cctacaagcaggggcagaaccagctctacaacgaactcaatcttggtcggagagaggagtacgacgtgctggacaagcggagaggac

gggacccagaaatgggggggaagccgcgcagaaagaatccccaagagggcctgtacaacgagctccaaaaggataagatggcagaa

gcctatagcgagattggtatgaaaggggaacgcagaagaggcaaaggccacgacggactgtaccagggactcagcaccgccaccaa

ggacacctatgacgctcttcacatgcaggccctgccgcctcgg.
```

A fifth aspect of the disclosure provides an expression vector, the expression vector is inserted with an expression cassette, the expression cassette includes a first nucleic acid fragment encoding an antigen binding molecule and a second nucleic acid fragment encoding an intracellular signaling molecule, the intracellular signaling molecule contains the truncated body of IL7Rα according to the first aspect, and an IRES element or a 2 A peptide coding sequence is inserted between the first nucleic acid fragment and the second nucleic acid fragment; and preferably, the expression cassette is the fusion nucleic acid according to the fourth aspect.

A sixth aspect of the disclosure provides a cell expressing a chimeric antigen receptor, the cell expressing a chimeric antigen receptor is obtained by transfection of the expression vector according to the fifth aspect by a host cell, and the chimeric antigen receptor contains the truncated body of IL7Rα according to the first aspect.

Optionally, the host cell is a T cell.

A seventh aspect of the disclosure provides use of the truncated body of IL7Rα according to the first aspect, the nucleic acid according to the second aspect, the fusion protein according to the third aspect, the fusion nucleic acid according to the fourth aspect, the expression vector according to the fifth aspect, and the cell expressing a chimeric antigen receptor according to the sixth aspect in preparation of a medication for treating a tumor.

Optionally, the tumor is glioma.

An eighth aspect of the disclosure provides a pharmaceutical composition, an active ingredient of which includes the cell expressing a chimeric antigen receptor containing the truncated body of IL7Rα according to the sixth aspect.

The disclosure is further described by the following examples, but the disclosure is not limited thereby.

Example 1

This example was used to explain the construction of expression vectors.

(1) Nucleotide sequences shown in SEQ ID NO. 4, SEQ ID NO. 5 and SEQ ID NO. 6 were respectively synthesized by using a full sequence synthesis method. The nucleotide sequence shown in SEQ ID NO. 4 was used for encoding a fusion protein shown in SEQ ID NO. 3. The nucleotide sequence shown in SEQ ID NO. 5 was used for encoding a fusion protein shown in SEQ ID NO. 7. The nucleotide sequence shown in SEQ ID NO. 6 was used for encoding a fusion protein shown in SEQ ID NO. 8. The compositions of the fusion proteins shown in SEQ ID NO. 3, SEQ ID NO. 7 and SEQ ID NO. 8 were as follows:

G1: the fusion protein shown in SEQ ID NO. 3 consisted of an anti-CD44 single-chain antibody, an anti-CD133 single-chain antibody, a CD28, a truncated body of IL7Rα, and a CD3;

G2: the fusion protein shown in SEQ ID NO. 7 consisted of an anti-CD44 single-chain antibody, an anti-CD133 single-chain antibody, a CD28, and a CD3;

G3: the fusion protein shown in SEQ ID NO. 8 consisted of an anti-CD44 single-chain antibody, an anti-CD133 single-chain antibody, a CD28, an IL7Rα, and a CD3.

The amino acid sequence of the fusion protein shown in SEQ ID NO. 7 was as follows:

```
QVQLVESGGGVVQPGRSLRLSCAASGFTFSSYGMHWVRQAPGKGLEWVA

VIWYDGSNKFYADSVKGRFTISRDNSKNTLYLQMNSLRAEDTAVYYCAR

RSDYRGYYGMDVWGQGTTVTVSSGSTSGGGSGGGSGGGGSSEIVLTQSP

ATLSLSPGERATLSCRASQSVINYLAWYQQKPGQAPRLLIYDASNRASG

IPARFSGSGSGTDFTLTISSLEPEDFAVYYCQQRRNWPLTFGGGTKVEI

KGGGGSGGGGSGGGGSQVQLVQSGAEVKKPGASVKVSCKASGYTFTDFE
```

-continued

MHWVRQAPGQGLEWMGDIDPGTGDTAYNLKFKGRVTMTTDTSTSTAYME

LRSLRSDDTAVYYCALGAFVYWGQGTLVTVSSGSTSGGGSGGGSGGGGS

SDVVMTQSPLSLPVTPGEPASISCRSSQSLANSYGNTYLSWYLQKPGQS

PQLLIYGISNRFSGVPDRFSGSGSGTDFTLKISRVEAEDVGVYYCLQGT

HQPYTFGQGTKLEIKTTTPAPRPPTPAPTIASQPLSLRPEACRPAAGGA

VHTRGLDFACDIYIWAPLAGTCGVLLLSLVITLYCRSKRSRLLHSDYMN

MTPRRPGPTRKHYQPYAPPRDFAAYRSRVKFSRSADAPAYKQGQNQLYN

ELNLGRREEYDVLDKRRGRDPEMGGKPRRKNPQEGLYNELQKDKMAEAY

SEIGMKGERRRGKGHDGLYQGLSTATKDTYDALHMQALPPR.

-continued

RSDYRGYYGMDVWGQGTTVTVSSGSTSGGGSGGGSGGGGSSEIVLTQSP

ATLSLSPGERATLSCRASQSVINYLAWYQQKPGQAPRLLIYDASNRASG

IPARFSGSGSGTDFTLTISSLEPEDFAVYYCQQRRNWPLTFGGGTKVEI

KGGGGSGGGGSGGGGSQVQLVQSGAEVKKPGASVKVSCKASGYTFTDFE

MHWVRQAPGQGLEWMGDIDPGTGDTAYNLKFKGRVTMTTDTSTSTAYME

LRSLRSDDTAVYYCALGAFVYWGQGTLVTVSSGSTSGGGSGGGSGGGGS

SDVVMTQSPLSLPVTPGEPASISCRSSQSLANSYGNTYLSWYLQKPGQS

PQLLIYGISNRFSGVPDRFSGSGSGTDFTLKISRVEAEDVGVYYCLQGT

HQPYTFGQGTKLEIKTTTPAPRPPTPAPTIASQPLSLRPEACRPAAGGA

The nucleotide sequence shown in SEQ ID NO. 5 was as follows:

caggtgcagctggtggagtctgggggaggcgtggtccagcctgggaggtccctgagactctcctgtgcagcgtctggattc accttcagtagctatggcatgcactgggtccgccaggctccaggcaaggggctggagtgggtggcagttatatggtatgatggaagtaat aaattctatgcagactccgtgaagggccgattcaccatctccagagacaattccaagaacacgctgtatctgcaaatgaacagcctgagag ccgaggacacggctgtgtattactgtgcgaggagaagtgactacaggggctactacggtatggacgtctggggccaagggaccacggt caccgtctcctcaggcagtactagcggtggtggctccgggggcggttccggtgggggcggcagcagcgaaattgtgttgacacagtctc cagccaccctgtctttgtctccaggggaaagagccaccctctcctgcagggccagtcagagtgttatcaactacttagcctggtaccaaca gaaacctggccaggctcccaggctcctcatctatgatgcatccaacagggcctctggcatcccagccaggttcagtggcagtgggtctgg gacagacttcactctcaccatcagcagcctagagcctgaagattttgcagtttattactgtcagcagcgtcgcaactggccgctcactttcgg cggagggaccaaggtggagatcaaaggaggtggtggatccggaggtggtggctccggaggtggtggatcccaggttcagctggtgca gtctggagctgaggtgaagaagcctggggcctcagtgaaggtctcctgcaaggcttctggttacacctttaccgactttgaaatgcactggg tgcgacaggcccctggacaagggcttgagtggatgggagatattgatcctggaactggtgatactgcctacaatctgaagttcaagggca gagtcaccatgaccacagacacatccacgagcacagcctacatggagctgaggagcctgaggtctgacgacacggccgtgtattactgt gcgttgggggcctttgtttactggggccagggaaccctggtcaccgtctcctcaggcagtactagcggtggtggctccgggggcggttcc ggtgggggcggcagcagcgatgttgtgatgactcagtctccactctccctgcccgtcacccctggagagccggcctccatctcctgcagg tctagtcagagtcttgcaaacagttatgggaacacctatttgtcttggtacctgcagaagccagggcagtctccacagctcctgatctatggg atttccaacagattttctggggtccctgacaggttcagtggcagtggatcaggcacagattttacactgaaaatcagcagagtggaggctga ggacgttggggtttattactgcttacaaggtacacatcagccgtacacgtttggccaggggaccaagctggagatcaaaaccactacccca gcaccgaggccacccaccccggctcctaccatcgcctcccagcctctgtccctgcgtccggaggcatgtagacccgcagctggtgggg ccgtgcatacccggggtcttgacttcgcctgcgatatctacatttgggcccctctggctggtacttgcggggtcctgctgctttcactcgtgat cactctttactgtaggagtaagaggagcaggctcctgcacagtgactacatgaacatgactccccgccgccccgggcccacccgcaagc attaccagccctatgccccaccacgcgacttcgcagcctatcgctcccgcgtgaaattcagccgcagcgcagatgctccagcctacaagc aggggcagaaccagctctacaacgaactcaatcttggtcggagagaggagtacgacgtgctggacaagcggagaggacgggaccca gaaatgggcgggaagccgcgcagaaagaatccccaagagggcctgtacaacgagctccaaaaggataagatggcagaagcctatagc gagattggtatgaaaggggaacgcagaagaggcaaaggccacgacggactgtaccagggactcagcaccgccaccaaggacacctat gacgctcttcacatgcaggccctgccgcctcgg.

The amino acid sequence of the fusion protein shown in SEQ ID NO. 8 was as follows:

QVQLVESGGGVVQPGRSLRLSCAASGFTFSSYGMHWVRQAPGKGLEWVA

VIWYDGSNKFYADSVKGRFTISRDNSKNTLYLQMNSLRAEDTAVYYCAR

-continued

VHTRGLDFACDIYIWAPLAGTCGVLLLSLVITLYCRSKRSRLLHSDYMN

MTPRRPGPTRKHYQPYAPPRDFAAYRSKKRIKPIVWPSLPDHKKTLEHL

CKKPRKNLNVSFNPESFLDCQIHRVDDIQARDEVEGFLQDTFPQQLEES

-continued

EKQRLGGDVQSPNCPSEDVVITPESFGRDSSLTCLAGNVSACDAPILSP

SRSLDCRESGKNGPHVYQDLLLSLGTTNSTLPPPFSLQSGILTLNPVAQ

GQPILTSLGSNQEEAYVTMSSFYQNQRVKFSRSADAPAYKQGQNQLYNE

-continued

LNLGRREEYDVLDKRRGRDPEMGGKPRKNPQEGLYNELQKDKMAEAYSE

IGMKGERRRGKGHDGLYQGLSTATKDTYDALHMQALPPR.

The nucleotide sequence shown in SEQ ID NO. 6 was as follows:

caggtgcagctggtggagtctgggggaggcgtggtccagcctgggaggtccctgagactctcctgtgcagcgtctggattc accttcagtagctatggcatgcactgggtccgccaggctccaggcaaggggctggagtgggtggcagttatatggtatgatggaagtaat aaattctatgcagactccgtgaagggccgattcaccatctccagagacaattccaagaacacgctgtatctgcaaatgaacagcctgagag ccgaggacacggctgtgtattactgtgcgaggagaagtgactacaggggctactacggtatggacgtctggggccaagggaccacggt caccgtctcctcaggcagtactagcggtggtggctccgggggcggttccggtgggggcggcagcagcgaaattgtgttgacacagtctc cagccaccctgtctttgtctccaggggaaagagccaccctctcctgcagggccagtcagagtgttatcaactacttagcctggtaccaaca gaaacctggccaggctcccaggctcctcatctatgatgcatccaacagggcctctggcatcccagccaggttcagtggcagtgggtctgg gacagacttcactctcaccatcagcagcctagagcctgaagattttgcagtttattactgtcagcagcgtcgcaactggccgctcactttcgg cggagggaccaaggtggagatcaaaggaggtggtggatccggaggtggtggctccggaggtggtggatcccaggttcagctggtgca gtctggagctgaggtgaagaagcctggggcctcagtgaaggtctcctgcaaggcttctggttacacctttaccgactttgaaatgcactggg tgcgacaggcccctggacaagggcttgagtggatgggagatattgatcctggaactggtgatactgcctacaatctgaagttcaagggca gagtcaccatgaccacagacacatccacgagcacagcctacatggagctgaggagcctgaggtctgacgacacggccgtgtattactgt gcgttgggggcctttgtttactggggccagggaaccctggtcaccgtctcctcaggcagtactagcggtggtggctccgggggcggttcc ggtgggggcggcagcagcgatgttgtgatgactcagtctccactctccctgcccgtcacccctggagagccggcctccatctcctgcagg tctagtcagagtcttgcaaacagttatgggaacacctatttgtcttggtacctgcagaagccagggcagtctccacagctcctgatctatggg atttccaacagattttctggggtccctgacaggttcagtggcagtggatcaggcacagattttacactgaaaatcagcagagtggaggctga ggacgttggggtttattactgcttacaaggtacacatcagccgtacacgtttggccaggggaccaagctggagatcaaaaccactacccca gcaccgaggccacccaccccggctcctaccatcgcctcccagcctctgtccctgcgtccggaggcatgtagacccgcagctggtgggg ccgtgcatacccggggtcttgacttcgcctgcgatatctacatttgggcccctctggctggtacttgcggggtcctgctgctttcactcgtgat cactctttactgtaggagtaagaggagcaggctcctgcacagtgactacatgaacatgactccccgccgccccgggcccacccgcaagc attaccagccctatgccccaccacgcgacttcgcagcctatcgctccaaaaaaaggattaagcctatcgtatggcccagtctccccgatcat aagaagactctggaacatctttgtaagaaaccaagaaaaaatttaaatgtgagtttcaatcctgaaagtttcctggactgccagattcataggg tggatgacattcaagctagagatgaagtggaaggttttctgcaagatacgtttcctcagcaactagaagaatctgagaagcagaggcttgga ggggatgtgcagagccccaactgcccatctgaggatgtagtcatcactccagaaagctttggaagagattcatccctcacatgcctggctg ggaatgtcagtgcatgtgacgcccctattctctccccttccaggtccctagactgcagggagagtggcaagaatgggcctcatgtgtacca ggacctcctgcttagccttgggactacaaacagcacgctgccccctccattttctctccaatctggaatcctgacattgaacccagttgctca gggtcagcccattcttacttccctgggatcaaatcaagaagaagcatatgtcaccatgtccagcttctaccaaaaccagcgcgtgaaattca gccgcagcgcagatgctccagcctacaagcaggggcagaaccagctctacaacgaactcaatcttggtcggagagaggagtacgacgt gctggacaagcggagaggacgggacccagaaatgggcgggaagccgcgcagaaagaatccccaagagggcctgtacaacgagctc caaaaggataagatggcagaagcctatagcgagattggtatgaaaggggaacgcagaagaggcaaaggccacgacggactgtaccag ggactcagcaccgccaccaaggacacctatgacgctcttcacatgcaggccctgccgcctcgg.

(2) The three nucleotide sequences synthesized in step (1) were respectively inserted into pLVX-IRES-ΔNGFR (purchased from Clontech Company, article number 631982) as a vector to obtain three kinds of lentivirus expression vectors of this example.

Example 2

This example was used to explain the preparation and test of T cells expressing a chimeric antigen receptor.

(1) The three kinds of lentivirus expression vectors constructed in Example 1 and an empty pLVX-IRES-ΔNGFR vector were packaged with lentiviruses respectively, and then T cells were cultured in vitro, transfected and proliferated according to the following methods.

(2) T cells in blood were separated according to the following method: 1 mL of sterile PBS and 1 mL of blood were mixed evenly, then slowly added to an upper layer of a lymphocyte separation medium Ficoll, and centrifuged at 4° C. and 400 g for 30 min, with acceleration and deceleration set to 0 respectively. After centrifugation, the upper plasma was removed, the middle white membrane cells were pipetted, PBS was added for re-suspension washing, and centrifugation was carried out for 10 min at 100 g, with normal acceleration and deceleration. After centrifugation, the upper washing solution was removed, 1 mL of 1640+10% FBS+1% double antibody+1×Glutamine medium was added to re-suspend cells, and then the cells were stimulated to proliferate by means of anti-human CD3/CD28 magnetic beads (purchased from Thermo Fisher company), where the concentration of re-suspended cells was $1\times10^6$ cells/mL and the amount of magnetic beads added was 100 μL. Then 100 IU/mL rhIL-2 (Peprotech) was added to stimulate culture for 2 days to obtain T cells.

(3) Transfection of lentiviruses was carried out according to the following method: the lentiviruses packaged in step (1) were respectively added to four parts of T cells separated above, and then polybrene with a final concentration of 6 μg/mL was added, followed by uniform mixing and centrifugation at 32° C. and 800 g for 100 min. After centrifugation, the culture was continued in an incubator for 24 h. After the culture, the culture solution was centrifuged at 1500 rpm for 15 min, and the centrifuged cells were inoculated at a density of $1\times10^6$/mL into a culture plate and stimulated for culture with rhIL2-100 IU/mL. After that, the medium was changed every 2-3 days until 2-4 weeks, and transfected T lymphocytes CAR-T 1, CAR-T 2, CAR-T 3 and CAR-T 4 were obtained. CAR-T 1 was transfected with the nucleotide sequence shown in SEQ ID NO. 4 and could express the fusion protein shown in SEQ ID NO. 3; CAR-T 2 was transfected with the nucleotide sequence shown in SEQ ID NO. 5 and could express the fusion protein shown in SEQ ID NO. 7; CAR-T 3 was transfected with the nucleotide sequence shown in SEQ ID NO. 6 and could express the fusion protein shown in SEQ ID NO. 8; and CAR-T 4 was transfected with the empty vector.

After culture, the cells were re-suspended with PBS, and the ratio of the above four kinds of transfected T lymphocytes and the expression of CAR protein on the surface were tested with a flow cytometer. The test method was as follows: the T cells to be tested after transfection were centrifuged and collected respectively, the supernatant was discarded after the T cells to be tested were washed with PBS once, and a corresponding test amount of monoclonal antibody was added according to antibody instructions and avoided light for 30 min, followed by PBS washing, re-suspension, filtration with a membrane, and sandwich test with a flow cytometer, where the antibody used for the test was a mixture of His-tag labeled CD44 and PE labeled anti-His-tag antibody. The results were shown in FIGS. 1-4.

Figure 2:
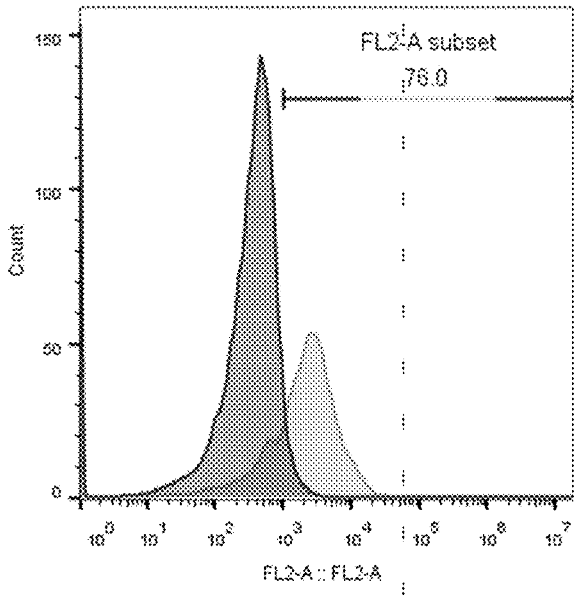
FIG. 2 is a flow cytometry test result diagram of CAR-T 2 cells provided by an embodiment of the disclosure.
Figure 3:
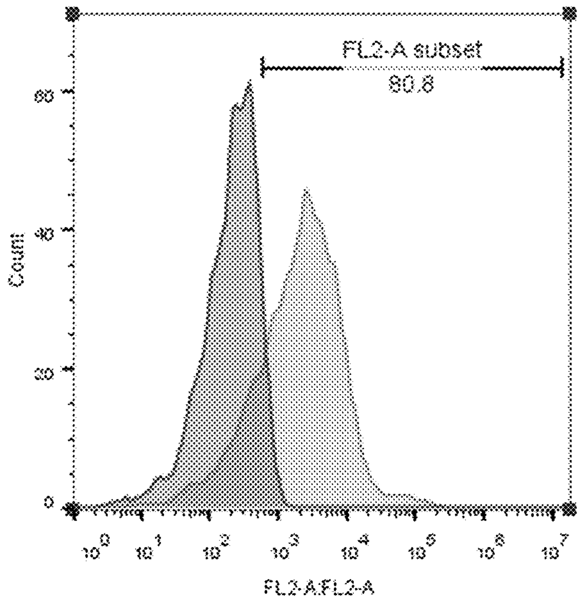
FIG. 3 is a flow cytometry test result diagram of CAR-T 3 cells provided by an embodiment of the disclosure.
Figure 4:
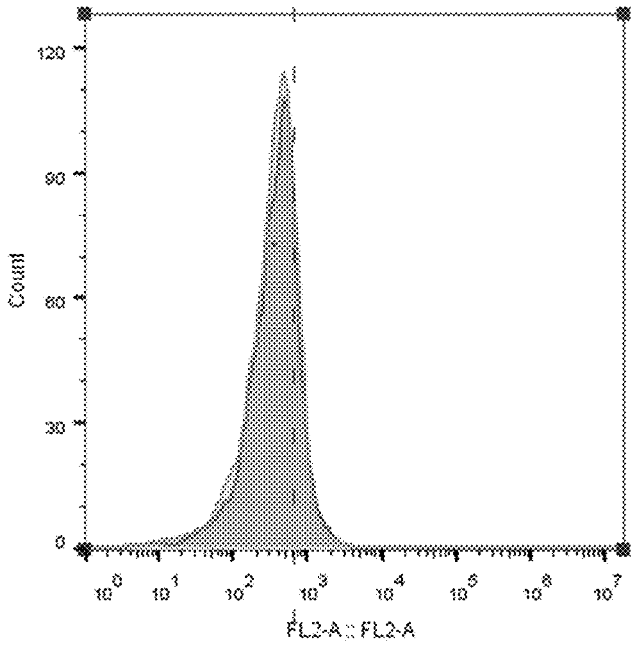
FIG. 4 is a flow cytometer test result diagram of CAR-T 4 cells according to an embodiment of the disclosure.

FIG. 1 is a flow cytometer test result diagram of CAR-T 1 cells according to an embodiment of the disclosure;

FIG. 2 is a flow cytometry test result diagram of CAR-T 2 cells according to an embodiment of the disclosure;

FIG. 3 is a flow cytometer test result diagram of CAR-T 3 cells according to an embodiment of the disclosure; and FIG. 4 is a flow cytometer test result diagram of CAR-T 4 cells according to an embodiment of the disclosure.

As can be seen from FIGS. 1-3, other cells different from normal T lymphocytes were detected out from the CAR-T 1 cells, the CAR-T 2 cells and the CAR-T 3 cells. As can be seen from FIG. 4, other cells different from normal T lymphocytes were not detected out from the CAR-T 4 cells. This showed that the CAR-T cells transfected with fusion genes in this example had successfully expressed the target fusion protein.

Example 3

This example was used to verify the proliferation capacity and survival of the CAR-T cells constructed in Example 2.

Four kinds of CAR-T cells obtained by transfection and culture in Example 2 were respectively mixed with CD44 and CD133 positive glioma stem cells GSC20 according to an effect-target ratio of 10 (the number of T cells: the number of glioma stem cells). The mixed cells were cultured in 24-well plates, where each well contained $10^5$ glioma stem cells, and the reaction system was 1 μL per well. The culture conditions included: 37° C., 5% $CO_2$, and culture in a saturated humidity incubator. After 0, 4, 8, 12, 18, and 26 days, different CAR-T cells were counted with cell counting plates to explore the proliferation of different CAR-T cells stimulated by target cells.

TABLE 1

| | Proliferation of different CAR-T cells stimulated by target cells ($\times10^6$) | | | | | |
|---|---|---|---|---|---|---|
| CAR-T cells | Day 0 | Day 4 | Day 8 | Day 12 | Day 18 | Day 26 |
| CAR-T 1 | 1.029 | 2.860 | 3.995 | 4.533 | 5.364 | 3.788 |
| CAR-T 2 | 1.147 | 2.435 | 3.151 | 3.080 | 0.665 | 0 |
| CAR-T 3 | 1.149 | 2.692 | 3.552 | 3.953 | 3.253 | 0 |
| CAR-T 4 | 1.135 | 2.494 | 2.999 | 0.464 | 0 | 0 |

As can be seen from Table 1, the CAR-T cells expressing the above-mentioned truncated body of IL7Rα had stronger proliferation capacity and longer survival.

Comparative Example

The CAR-T 1 cells obtained by transfection and culture in Example 2 and conventional second generation CAR-T cells (EGFR vIII-CD28-CD3) targeting a classical tumor target EGFR vIII were respectively mixed with CD44 positive and CD133 positive glioma stem cells GSC20 according to different effect-target ratios (the number of T cells: the number of glioma stem cells). The mixed cells were cultured in 96-well plates, where each well contained $4\times10^4$ glioma stem cells, and the reaction system was 200 μL per well. The culture conditions included: 37° C., 5% $CO_2$, and culture in a saturated humidity incubator for 4 h.

Determination of lactate dehydrogenase activity: after centrifugation, 100 μL of supernatant was aspirated from each well and placed in 96-well enzyme-labeled plates, 100 μL of LDH substrate was added to each well, and the reaction was carried out at room temperature for 30 min without light. After the reaction, 50 μL of termination solution was added to each well to terminate the enzymatic reaction. The optical density (OD) was measured at 490 nm with a microplate reader. The average optical density (OD) of each group was calculated, and the lysis rate of glioma stem cells by each kind of T cells was calculated according to the following formula. The results were shown in Table 1.

Lysis rate %=(OD of the experimental group−OD spontaneously released by glioma stem cells−OD naturally released by effector cells)/(maximum OD released by glioma stem cells−OD spontaneously released by glioma stem cells)

The test results were shown in Table 2.

TABLE 2

| | Lysis rate of glioma stem cells by conventional second generationn CAR-T cells under different effect-target ratios (%) | | | |
|---|---|---|---|---|
| Effect-target ratio | 5:1 | 3:1 | 2:1 | 1:1 |
| CAR-T 1 | 84.74% | 67.20% | 37.13% | 31.48% |
| Conventional CAR-T | 17.57% | 14.62% | 13.97% | 11.88% |

As can be seen from Table 2, the ability of the conventional second generation CAR-T cells targeting a classical tumor stem cell target EGFR vIII to kill glioma stem cells was weaker than that of the T cells expressing the truncated body of IL7Rα provided by the disclosure.

The preferred embodiments of the disclosure are described in detail above with reference to the accompanying drawings. However, the disclosure is not limited to the specific details in the above embodiments. Various simple variations may be made to the technical solutions of the disclosure within the scope of the technical idea of the disclosure, and these simple variations fall within the scope of the disclosure.

It should be further noted that the specific technical features described in the above specific embodiments may be combined in any suitable manner without contradiction. In order to avoid unnecessary repetition, the disclosure will not describe various possible combinations.

Moreover, the various different embodiments of the disclosure may be combined randomly without deviating from the idea of the disclosure, and the combinations should also be regarded as the disclosure of the disclosure.

What is claimed is:

1. A fusion protein comprising the amino acid sequence shown in SEQ ID NO: 3.

2. A fusion nucleic acid comprising the nucleotide sequence shown in SEQ ID NO: 4.

3. An expression vector comprising the fusion nucleic acid of claim 2.

4. A cell expressing a chimeric antigen receptor, wherein the cell is obtained by transfecting a host cell with the expression vector of claim 3, and wherein the chimeric antigen receptor comprises the amino acid sequence shown in SEQ ID NO. 3.

5. The cell according to claim 4, wherein the host cell is a T cell.

6. A pharmaceutical composition comprising the cell of claim 4.

7. The expression vector according to claim 3, wherein the fusion nucleic acid encodes a fusion protein, wherein the fusion protein contains an antigen binding domain, a transmembrane domain and an intracellular signaling domain that are sequentially linked; wherein the amino acid sequence of the intracellular signaling domain comprises the amino acid sequence of a truncated body of IL7Rα, wherein the amino acid sequence of the truncated body of IL7Rα is SEQ ID NO. 1.

* * * * *